(12) United States Patent
Huang et al.

(10) Patent No.: US 12,281,293 B1
(45) Date of Patent: Apr. 22, 2025

(54) BIOREACTOR EXHAUST SYSTEM

(71) Applicant: Ark Biotech Inc., Westwood, MA (US)

(72) Inventors: Zheng Huang, Bolton, MA (US); Kai Hoeffner, Medway, MA (US)

(73) Assignee: Ark Biotech Inc., Westwood, MA (US)

( * ) Notice: Subject to any disclaimer, the term of this patent is extended or adjusted under 35 U.S.C. 154(b) by 0 days.

(21) Appl. No.: 18/829,031

(22) Filed: Sep. 9, 2024

Related U.S. Application Data

(60) Provisional application No. 63/590,327, filed on Oct. 13, 2023.

(51) Int. Cl.
*C12M 1/00* (2006.01)
*C12M 1/02* (2006.01)
*C12M 1/12* (2006.01)
*C12M 1/34* (2006.01)
*C12M 1/36* (2006.01)

(52) U.S. Cl.
CPC ............ *C12M 29/20* (2013.01); *C12M 37/00* (2013.01); *C12M 41/18* (2013.01); *C12M 41/30* (2013.01); *C12M 41/40* (2013.01); *C12M 41/44* (2013.01); *C12M 41/48* (2013.01)

(58) Field of Classification Search
None
See application file for complete search history.

(56) References Cited

U.S. PATENT DOCUMENTS

2008/0173176 A1\* 7/2008 Duesel ................ B01D 47/021
422/176
2010/0316534 A1\* 12/2010 Niazi ...................... A61L 9/145
422/122

FOREIGN PATENT DOCUMENTS

| CA | 3026747 C | \* | 5/2022 | ........ A61M 16/0488 |
| CN | 201940137 U | \* | 8/2011 | |
| CN | 113101402 A | \* | 7/2021 | ............... A61L 2/18 |
| EP | 0514259 A1 | \* | 11/1992 | |

\* cited by examiner

*Primary Examiner* — William H. Beisner
(74) *Attorney, Agent, or Firm* — Van Pelt, Yi & James LLP

(57) ABSTRACT

A bioreactor exhaust system includes an exhaust tube, a shut off valve, and a vessel. The exhaust tube includes a level sensor. The vessel includes a sterilant. The shut off valve is responsive to the sterilant reaching the level sensor.

21 Claims, 4 Drawing Sheets

BIOREACTOR EXHAUST SYSTEM

CROSS REFERENCE TO OTHER APPLICATIONS

This application claims priority to U.S. Provisional Patent Application No. 63/590,327 entitled BIOREACTOR EXHAUST SYSTEM filed Oct. 13, 2023 which is incorporated herein by reference for all purposes.

BACKGROUND OF THE INVENTION

In a conventional cell culture bioreactor, various gases are continuously introduced to bioreactor vessel through headspace and/or spargers. A mixture of exhaust gas has to be vented through a vent filter, such as a vent filter 102 seen in FIGS. 1A and 1B. The vent filter serves as a sterile boundary to protect the cell culture from contamination. The vent filter housing 104 needs to be cleaned before installing a new filter. The new filter, housing, and piping also need to be sterilized before cell culture can commence.

The exhaust gas contains moisture and small droplets of cell culture media. The droplets and condensed moisture can wet or foul the vent filter over time, causing pressure buildup or contamination. To mitigate the risk of wet/foul vent filters, several methods are often implemented, e.g., exhaust condenser, heated exhaust pipe, heated filter housing, dual filters, etc. Although these methods result in various degrees of success, they do not completely solve the wet/fouling filter problem and it is quite common that the vent filters need to be replaced during cell culture run, which can be disruptive/expensive.

In addition to the risk of contamination, a wet or fouled vent filter poses a safety risk that jeopardizes the integrity of the bioreactor vessels, whether they are single-use, glass, or stainless steel. Additional monitoring is often implemented to continuously monitor the pressure drop across the vent filter.

Moreover, vent filters are single-use and have to be discarded after each bioreactor run, adding significant cost to cell culture operation. Lastly, a vent filter may be plugged during a batch. As a result, the entire batch needs to be shut down or the vent filter needs to be replaced on the fly, which is a hassle and a risky operation.

BRIEF DESCRIPTION OF THE DRAWINGS

Various embodiments of the invention are disclosed in the following detailed description and the accompanying drawings.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Bioreactor exhaust systems are disclosed herein. The bioreactor exhaust systems establish an aseptic boundary and safely vent the exhaust gas from a bioreactor without using a vent filter. The bioreactor exhaust systems disclosed herein eliminate the need for costly vent filters associated with conventional cell culture bioreactors, while also reducing contamination and safety risk from fouled filters.

Figure 1B:
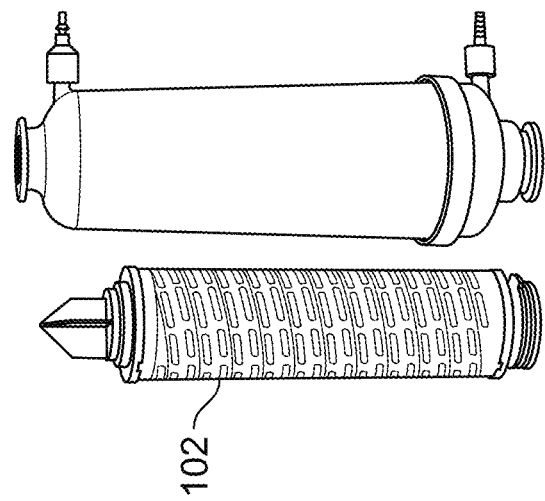
FIGS. 1A and 1B illustrate examples of a vent filter.
Figure 1A:
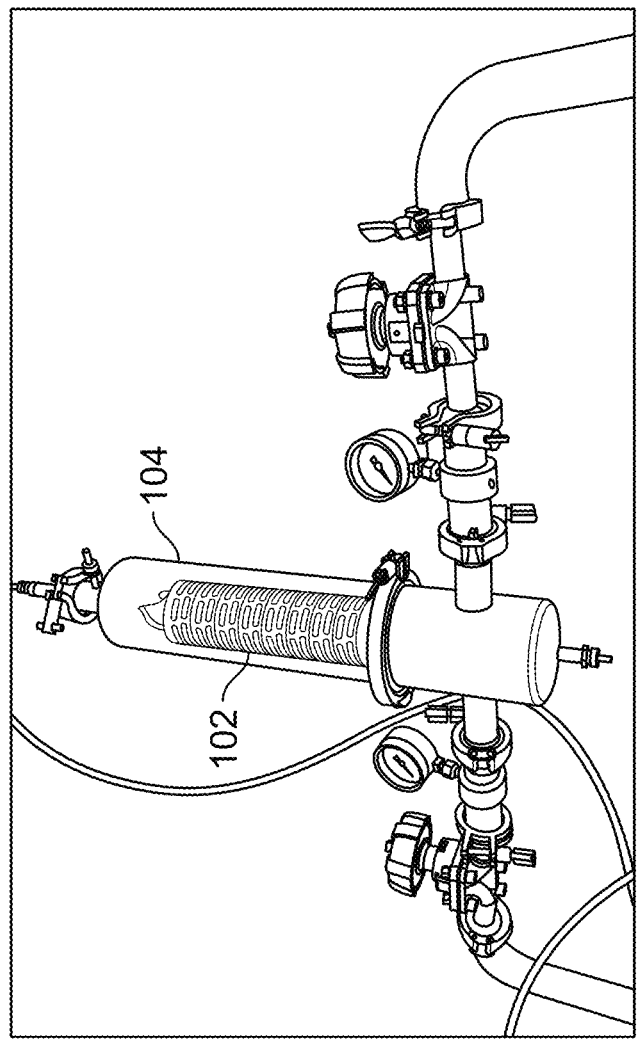
Figures 2, 3:
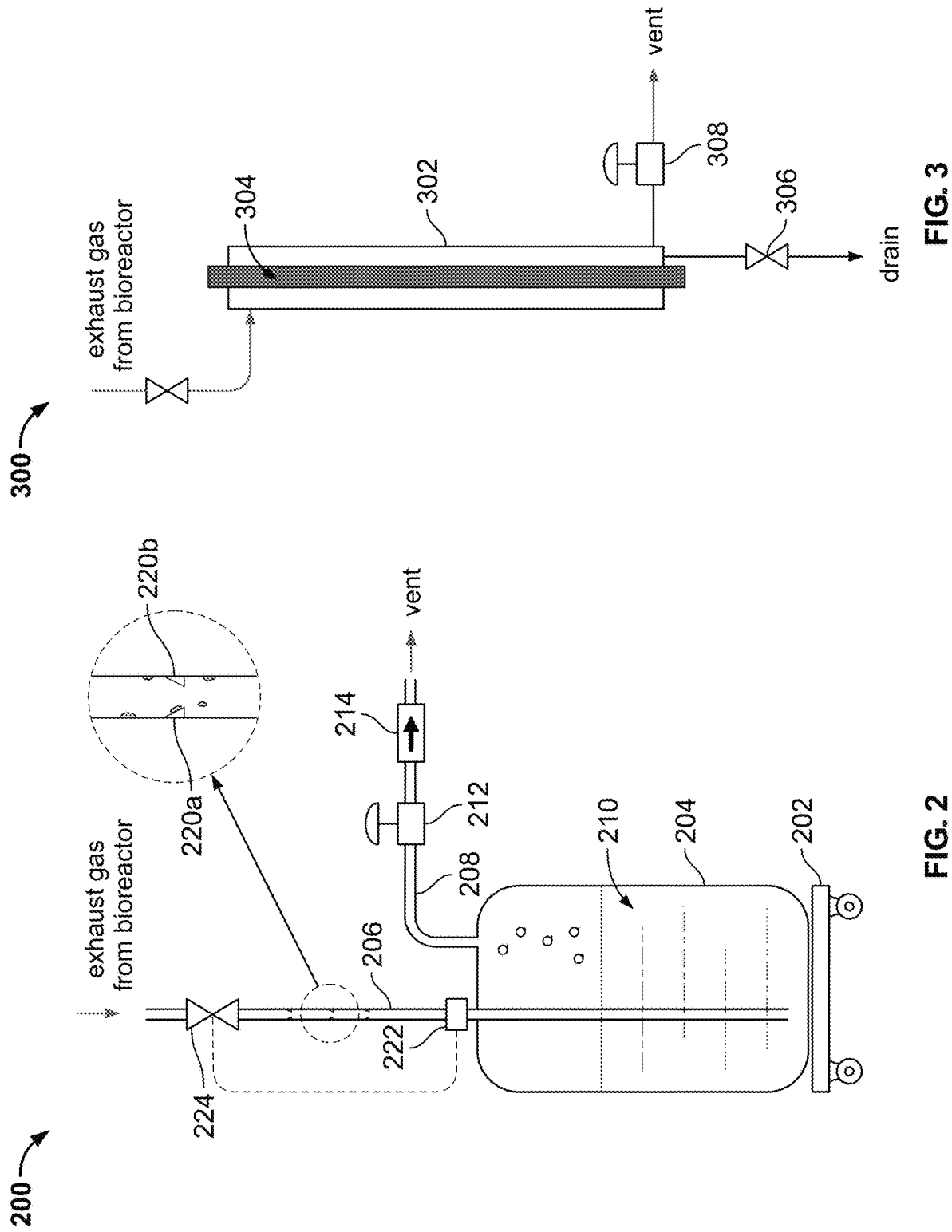
FIG. 2 is a diagram illustrating a bioreactor exhaust system in accordance with some embodiments.
FIG. 3 is a diagram illustrating a bioreactor exhaust system in accordance with some embodiments.

FIG. 2 is a diagram illustrating a bioreactor exhaust system in accordance with some embodiments. In the example shown, the bioreactor exhaust system 200 includes vessel 204 that is located on a platform 202 having a plurality of wheels. A top portion of vessel 204 includes a first opening through which exhaust tube 206 (e.g., dip tube) passes. The top portion of vessel 204 includes a second opening coupled to an exhaust vent conduit 208.

Vessel 204 stores sterilant 210. In some embodiments, sterilant 210 is a strong base, such as sodium hydroxide, potassium hydroxide, or calcium hydroxide. In some embodiments, sterilant 210 is ethanol, isopropanol alcohol, hydrogen peroxide, sodium hypochlorite, peracetic acid, etc. Sterilant 210 may be mixed with an antifoam agent, such as a silicone-based defoamer or a polyether-based defoamer to prevent foam out and the accumulation of bubbles. In some embodiments, ozone or chlorine dioxide gas could be sparged into aqueous solution to serve as a sterilant.

The exhaust gas from the bioreactor enters the bioreactor exhaust system 200 via exhaust tube 206 and enters sterilant 210. The exhaust gas includes moisture and small droplets of cell culture media. The chemical composition of sterilant 210 is configured to prevent contamination in the bioreactor by killing or preventing any contaminants (e.g., bacteria, fungi, etc.). The exhaust gas bubbles to the surface of sterilant 210 and exits bioreactor exhaust system 200 via exhaust vent conduit 208.

The exhaust vent 208 includes pressure control valve 212 and check valve 214. Pressure control valve 212 is configured to control the pressure inside vessel 204. Check valve 214 is configured to prevent the backflow of unfiltered air into bioreactor exhaust system 200. In the event that check valve 214 fails to prevent the backflow of unfiltered air, the unfiltered air enters the headspace of vessel 204. Any bacteria included in the unfiltered air is killed by sterilant 210 before they could make their way to the bioreactor. In the rare event that bacteria is not killed by sterilant 210, it will not be able to enter the bioreactor via the walls of exhaust tube 206 because condensate forms on the walls of tube 206 and gravity causes water droplets that are on the walls of exhaust tube 206 to fall into sterilant 210.

In some embodiments, tube 206 has a textured interior wall to prevent discourage condensate droplets from coalescing with each other, and to prevent contamination from droplets migrating back to the bioreactor. In some embodiments, the textured interior wall includes one or more sets of a plurality of rings with a cross-section shaped like ramps, such as ramps 220a, 220b, or other shapes designed to cause the condensate droplets to drop into sterilant 210.

Exhaust tube 206 includes a level sensor 222 and a shut-off valve 224. Level sensor 222 may be an ultrasonic, optical, conductivity, or other type of level sensor. Pressure control valve 212 is configured to control the pressure inside vessel 204. In some embodiments, pressure control valve 212 may fail. In some embodiments, there is a temperature change in the environment associated with bioreactor exhaust system 200. In these embodiments where the pressure and/or temperature changes, the level of sterilant 210 may rise within vessel 204. In response detecting the level of sterilant 210 at a particular level within vessel 204, level sensor 222 is configured to provide an output to shut off valve 224 that causes shut off valve 224 to close. This prevents the bioreactor from becoming contaminated with sterilant 210 and killing cells in the bioreactor. In some embodiments, a sprayball is located within vessel 204 in a similar manner to sprayball 410.

FIG. 3 is a diagram illustrating a bioreactor exhaust system in accordance with some embodiments. In the example shown, bioreactor exhaust system 300 includes exhaust tube 302 and ultraviolet light tube 304. Ultraviolet light tube 304 acts as an aseptic barrier in place of or in addition to sterilant 210. UV light is known to effectively kill contaminants (e.g., bacteria, fungi, yeast, etc) from the environment should they make their way into the exhaust gas. The moisture and small droplets of cell culture media included in the exhaust gas are removed from bioreactor exhaust system 300 via a sterile drain vessel when valve 306 is in an open state. The exhaust gas is removed from bioreactor exhaust system 300 via a vent when pressure control valve 308 is in an open state. In some embodiments, a check valve (not shown) is located between pressure control valve 308 and the vent.

Although FIG. 3 does not depict exhaust tube 302 having a textured interior wall, exhaust tube 302 may have a textured interior wall similar to the textured interior wall depicted in FIG. 2. In some embodiments, bioreactor exhaust system 200 incorporates the ultraviolet light tube 304 from FIG. 3 into exhaust tube 206. In some embodiments, ultraviolet light tube 304 is located between level sensor 222 and shut off valve 224. The ultraviolet light tube 304 may be located between the level sensor 222 and a bottom set of the ramp-shaped ring textures or other shapes designed to cause the condensate droplets to drop into sterilant 210. The ultraviolet light tube 304 may be located between shutoff valve 224 and a top set of the ramps or other shapes designed to cause the condensate droplets to drop into sterilant 210. The ultraviolet light tube 304 may be located between a first set of ramps or other shapes designed to cause the condensate droplets to drop into sterilant 210 and a second set of ramps or other shapes designed to cause the condensate droplets to drop into non-volatile sterilant 210. The ultraviolet light tube 304 may be located before shutoff valve 224.

Figure 4:
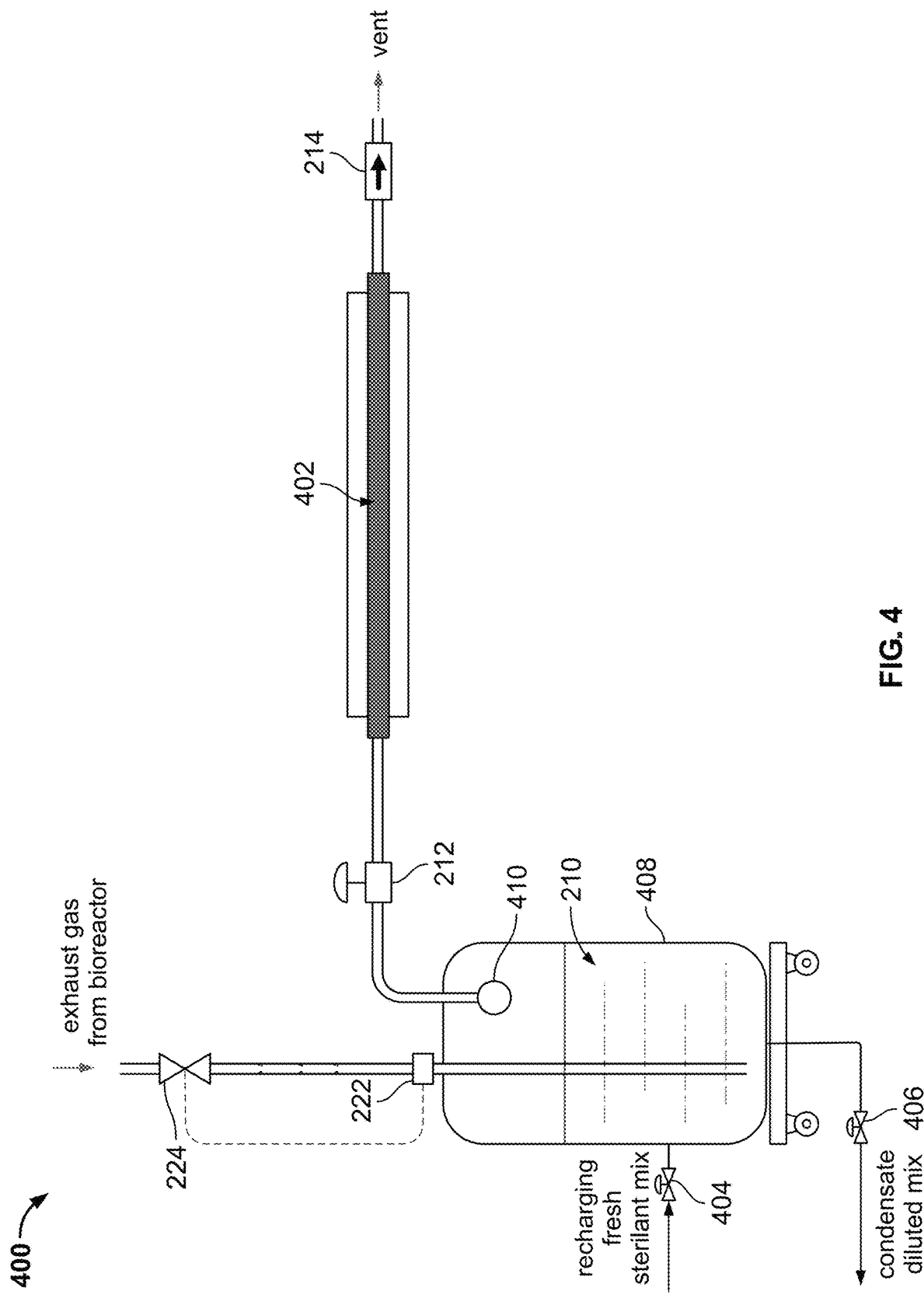
FIG. 4 is a diagram illustrating a bioreactor exhaust system in accordance with some embodiments.

FIG. 4 is a diagram illustrating a bioreactor exhaust system in accordance with some embodiments. In the example shown, bioreactor exhaust system 400 is similar to bioreactor exhaust system 200, except that the exhaust vent conduit also includes ultraviolet light tube 404.

Bioreactor exhaust system 400 also includes inlet valve 404 and outlet valve 406. Bioreactor exhaust system 200 may also include inlet valve 404 and outlet valve 406. A bioreactor is configured to run a batch for an extended period of time (e.g., 60 days perfusion run). Fresh sterilant may be introduced into the vessel via inlet valve 404. The diluted sterilant (e.g., sterilant 210 mixed with the moisture and small droplets of cell culture media) is removed from the vessel via outlet valve 406. Some of the volatile sterilant may evaporate during the batch. A fresh sterilant mix may be added during the batch to recharge the volatile sterilant. Bioreactor exhaust system 400 includes sprayball 410 to clean the vessel during a batch turn-around.

Figure 5:
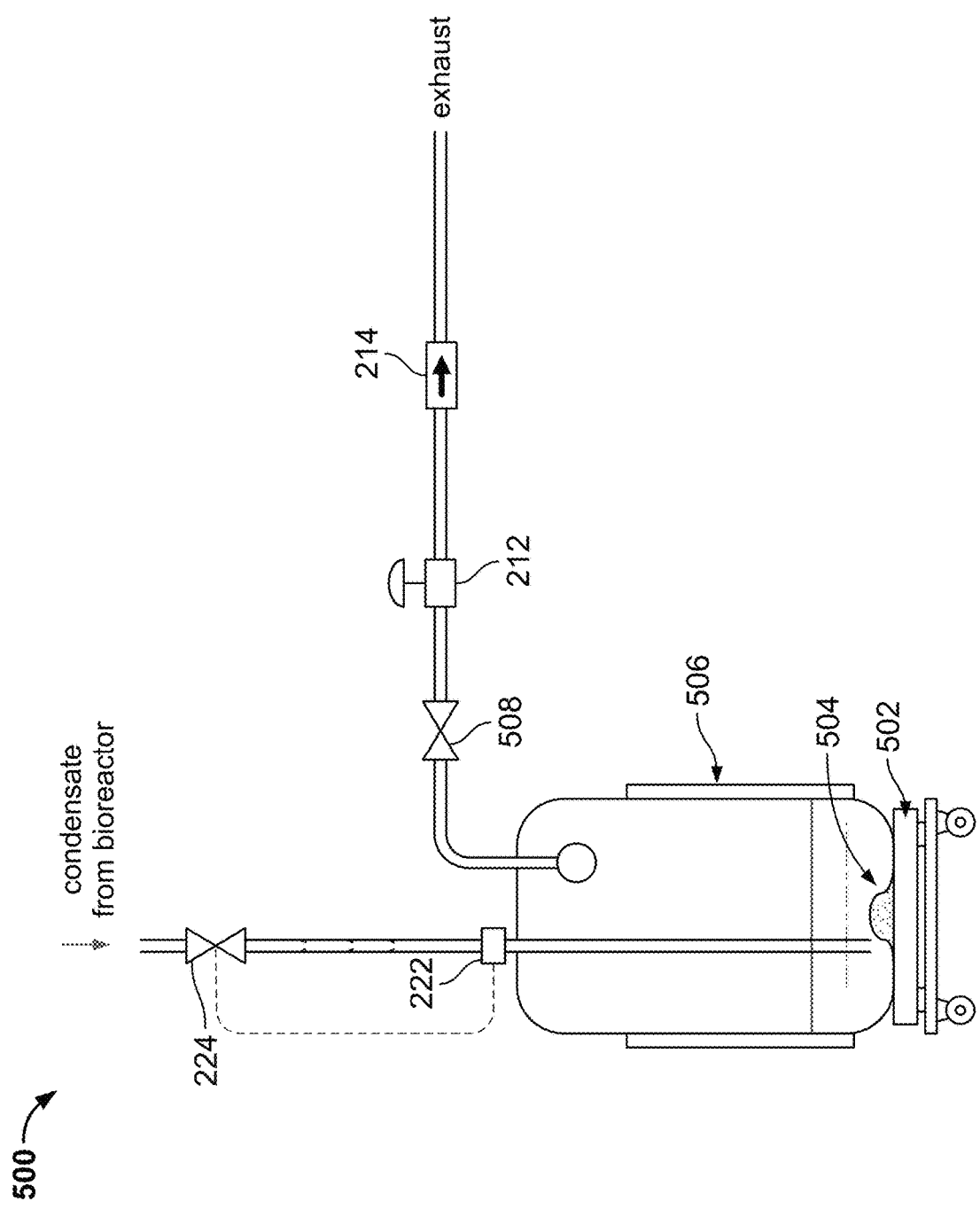
FIG. 5 is a diagram illustrating a bioreactor exhaust system in accordance with some embodiments.

FIG. 5 is a diagram illustrating a bioreactor exhaust system in accordance with some embodiments. In the example shown, bioreactor exhaust system 500 is similar to bioreactor exhaust system 200, except that the exhaust vent conduit also includes shut off valve 508, the vessel is situated on a monitoring device 502, the vessel is surrounded by a warming component 506. In some embodiments, monitoring device 502 is a weight scale, one or more load sensors, or a level sensor. In some embodiments, warming component 506 is a jacket or heating blanket that surrounds the vessel.

Sterilant refilling and overflow discharging add to operators' operational burden. Bioreactor exhaust system 500 may eliminate this burden. To achieve this objective, a temperature-controlled sterilant vessel and non-volatile sterilant, e.g., sodium hydroxide, are needed. Controlling the sterilant solution temperature ensures that no net accumulation of condensate occurs from the bioreactor exhaust stream, thereby eliminating operational complexity.

A powder or concentrate version of a non-volatile sterilant and antifoam agent 504 are added to the vessel before a steam-in-place (SIP) operation. The amount of the powder or concentrate version of the non-volatile sterilant depends on a setpoint weight for the non-volatile sterilant and antifoam agent 504, which can be measured by monitoring device 502. Near the end of the SIP cycle, but before the cooling step, shutoff valve 508 is closed. Because the vessel of the bioreactor exhaust system has a higher surface-to-volume ratio than the bioreactor, it will cool faster than the bioreactor vessel. As a result, it will continuously draw steam from the bioreactor vessel and condense it into water. Once the end of the exhaust dip tube is sufficiently submerged in the sterilant solution, shutoff valve 508 is opened, temperature control is turned on to ensure the sterilant weight reaches a setpoint and stays there until the end of the bioreactor run. The temperature of the vessel may be controlled by turning on/off warming component 506.

In some embodiments, the sterilant weight is above the setpoint. Based on an output of monitoring component 502, the warming component 506 may be turned on to cause some of the water in the non-volatile sterilant to evaporate and leave bioreactor exhaust system 500. In some embodiments, the sterilant weight is below the setpoint. Based on an output of monitoring component 502, the warming component 506 may be turned off to cause more condensate to collect in the vessel. Heating power of the warming component is controlled by a PID controller based on the weight associated with the sterilant.

SUMMARY

One or a combination of the four aseptic barriers could be used to replace a vent filter, thus greatly lower the (equipment and consumable) cost of cell culture. There is no concern of wet/foul and pressure build-up that often associated with vent filter.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A bioreactor exhaust system, comprising:
   an exhaust tube having a level sensor, wherein the exhaust tube is coupled to a bioreactor;
   a shut off valve located between the bioreactor and the level sensor; and
   a vessel having a sterilant, wherein the shut off valve is responsive to the sterilant reaching the level sensor.

2. The bioreactor exhaust system of claim 1, wherein the exhaust tube includes a plurality of shapes configured to cause condensate droplets to drop into the vessel.

3. The bioreactor exhaust system of claim 2, wherein the plurality of shapes are located between the shut off valve and the level sensor.

4. The bioreactor exhaust system of claim 1, further comprising an ultraviolet light located above the level sensor.

5. The bioreactor exhaust system of claim 4, wherein the ultraviolet light is located above the level sensor and the shut off valve.

6. The bioreactor exhaust system of claim 1, wherein the vessel includes an antifoam agent.

7. The bioreactor exhaust system of claim 1, further comprising an exhaust vent conduit.

8. The bioreactor exhaust system of claim 7, wherein the exhaust vent conduit includes a pressure control valve and a check valve.

9. The bioreactor exhaust system of claim 8, wherein an ultraviolet light is located between the pressure control valve and the check valve.

10. The bioreactor exhaust system of claim 1, wherein the vessel is connected to an inlet valve and an outlet valve.

11. The bioreactor exhaust system of claim 10, wherein fresh sterilant is added to the vessel via the inlet valve.

12. The bioreactor exhaust system of claim 10, wherein diluted sterilant is removed from the vessel via the outlet valve.

13. The bioreactor exhaust system of claim 1, wherein the level sensor is an ultrasonic sensor, optical, or conductivity sensor.

14. The bioreactor exhaust system of claim 1, wherein the sterilant is a non-volatile sterilant.

15. The bioreactor exhaust system of claim 14, wherein the non-volatile sterilant is sodium hydroxide.

16. The bioreactor exhaust system of claim 14, wherein a powder or concentrate version of the non-volatile sterilant is introduced into the vessel before a steam in place operation.

17. The bioreactor exhaust system of claim 1, wherein a warming component surrounds the vessel or inside the vessel.

18. The bioreactor exhaust system of claim 17, wherein the vessel is situated on a monitoring component that monitors a weight associated with the sterilant.

19. The bioreactor exhaust system of claim 18, wherein the warming component is turned on in response to the monitoring component determining that the weight associated with the sterilant is above a setpoint.

20. The bioreactor exhaust system of claim 18, wherein the warming component is turned off in response to the monitoring component determining that the weight associated with the sterilant is below a setpoint.

21. The bioreactor exhaust system of claim 18, wherein heating power of the warming component is controlled by a PID controller based on the weight associated with the sterilant.

* * * * *